(12) United States Patent
Takagaki et al.

(10) Patent No.: US 7,687,546 B2
(45) Date of Patent: Mar. 30, 2010

(54) QUATERNARY AMMONIUM COMPOUND, PROCESS FOR PRODUCING THE SAME, THERAPEUTIC AGENT FOR CEREBROVASCULAR DISORDER, AND THERAPEUTIC AGENT FOR HEART DISEASE

(75) Inventors: Hidetsugu Takagaki, Sakura (JP); Yoshiyuki Sano, Yotsukaido (JP); Yasuyuki Katakami, Chiba (JP); Masanori Miyamoto, Sakura (JP)

(73) Assignee: Activus Pharma Co., Ltd., Yotsukaido-shi (JP)

( * ) Notice: Subject to any disclaimer, the term of this patent is extended or adjusted under 35 U.S.C. 154(b) by 150 days.

(21) Appl. No.: 10/594,545

(22) PCT Filed: Mar. 29, 2005

(86) PCT No.: PCT/JP2005/005921

§ 371 (c)(1), (2), (4) Date: Jul. 2, 2008

(87) PCT Pub. No.: WO2005/095324

PCT Pub. Date: Oct. 13, 2005

(65) Prior Publication Data

US 2008/0269345 A1  Oct. 30, 2008

(30) Foreign Application Priority Data

Mar. 31, 2004 (JP) .............................. 2004-103737

(51) Int. Cl.
  *A01N 33/12* (2006.01)
  *A61K 31/14* (2006.01)
(52) U.S. Cl. ..................................................... 514/643
(58) Field of Classification Search ........................ None
  See application file for complete search history.

(56) References Cited

U.S. PATENT DOCUMENTS

| | | | |
|---|---|---|---|
| 3,740,397 A | | 6/1973 | Lafon |
| 3,801,641 A | * | 4/1974 | Payot et al. ................ 564/287 |
| 3,906,030 A | | 9/1975 | Castaigne |
| 4,933,103 A | | 6/1990 | Aoyagi et al. |
| 4,985,180 A | | 1/1991 | Bellis et al. |
| 2004/0010032 A1 | | 1/2004 | Biard |

FOREIGN PATENT DOCUMENTS

| | | | |
|---|---|---|---|
| GB | 9 19126 | * | 2/1963 |
| GB | 919126 | | 2/1963 |
| JP | 48-88218 | | 11/1973 |
| JP | 49-43936 | | 4/1974 |
| JP | 51-36256 | | 10/1976 |
| JP | 63-233969 | | 9/1988 |
| JP | 2-84499 | | 3/1990 |
| JP | 3-101645 | | 4/1991 |
| WO | WO-02/48078 | | 6/2002 |

OTHER PUBLICATIONS

Supplementary European Search Report dated Feb. 26, 2008 from the European Patent Office, issued on the European patent application No. 05 72 7867.3.
Tanezo Taguchi et al., "Organic Chemistry in Drug Production," Nanzando Co., Ltd., 1967, pp. 385; cover and back pages; and the English translation thereof.
Office Action mailed May 9, 2008, issued on the corresponding Chinese application and the English translation thereof.

* cited by examiner

*Primary Examiner*—Porfirio Nazario Gonzalez
*Assistant Examiner*—Chukwuma O Nwaonicha
(74) *Attorney, Agent, or Firm*—Edwards Angell Palmer & Dodge LLP

(57) ABSTRACT

A quaternary ammonium compound of the present invention is a quaternary ammonium compound represented by general formula (I) or (I')

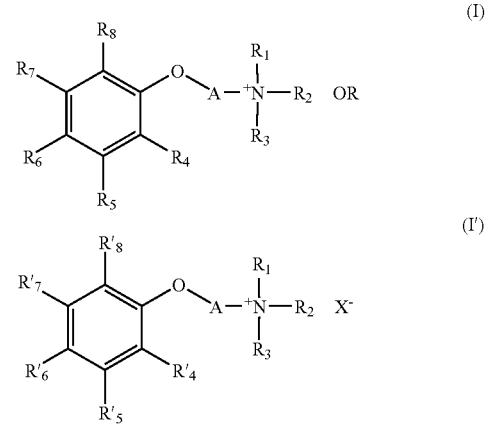

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$ to $R_3$ may be the same or different and represent a linear or branched alkyl group having 1 to 12 carbon atoms, one of $R_4$ to $R_8$ represents $CO_2^-$ or $SO_3^-$, while no more than three of the remaining $R_4$ to $R_8$ represent a group selected from the group consisting of a hydroxyl group and an alkoxy group having 1 to 4 carbon atoms, and other $R_4$ to $R_8$ represent a hydrogen atom, one of $R'_4$ to $R'_8$ represents $CO_2H$ or $SO_3H$, no more than three of the remaining $R'_4$ to $R'_8$ represent a group selected from a protected hydroxyl group and an alkoxy group having 1 to 4 carbon atoms, while other $R'_4$ to $R'_8$ represent a hydrogen atom, and $X^-$ represents an anion capable of forming a salt with a quaternary ammonium group).

18 Claims, No Drawings

QUATERNARY AMMONIUM COMPOUND, PROCESS FOR PRODUCING THE SAME, THERAPEUTIC AGENT FOR CEREBROVASCULAR DISORDER, AND THERAPEUTIC AGENT FOR HEART DISEASE

TECHNICAL FIELD

The present invention relates to a novel quaternary ammonium compound, a process for producing the same, and a therapeutic agent for cerebrovascular disorder and a therapeutic agent for heart disease having said quaternary ammonium compound as an active ingredient thereof.

BACKGROUND ART

Compounds in the form of [2-(4-methoxycarbonyl-phenoxy)-ethyl]-trimethylammonium and [2-(4-ethoxycarbonyl-phenoxy)-ethyl]-trimethylammonium are known (see UK Patent No. 919126).

A method for producing the aforementioned compounds in the case the quaternary ammonium group is a trimethylammonium group is described in which a phenol derivative is reacted with ethane dibromide in the presence of sodium metal, further reacted with dimethylamine, and treated with methyl iodide (see UK Patent No. 919126). In addition, a method for introducing a dimethylaminoethyl group, which is able to serve as a precursor of a quaternary ammonium group, is described in which a phenol derivative is reacted with 2-dimethylaminoethyl chloride in the presence of sodium metal (see German Patent No. 905738). Moreover, a method for introducing a dimethylaminoethyl group is described in which a phenol derivative is reacted with 2-dimethylaminoethyl chloride in the presence of a metal alcoholate (see M. B. Moore, J. Amer. Chem. Soc., 78:5633-5636 (1956)).

However, among the aforementioned compounds, a compound is not known which has a carboxyl group or sulfonyl group instead of an alkoxycarbonyl group in a benzene ring.

In addition, a production method has heretofore not been known for introducing a dialkylamino group, capable of serving as a precursor of a quaternary ammonium compound having a carboxyl group or sulfonyl group, at high yield by reacting with a sulfonic acid ester derivative in a certain specific solvent.

In addition, it has heretofore been completely unknown that a quaternary ammonium compound of the present invention has superior safety and demonstrates extremely superior effects as a cerebrovascular disease therapeutic agent and heart disease therapeutic agent.

DISCLOSURE OF THE INVENTION

An object of the present invention is to provide a specific quaternary ammonium compound in the form of a pharmaceutical having a high level of safety and superior effects, and particularly has superior effects on cerebrovascular disorder and heart disease.

As a result of studying a large number of compounds, the inventors of the present invention found that a specific quaternary ammonium compound has high levels of safety and pharmacological efficacy, and has superior effects on cerebrovascular disorder and heart disease, thereby leading to completion of the present invention.

In addition, as a result of conducting studies on various reaction conditions, the inventors of the present invention found an extremely superior process for producing the compound of the present invention.

Namely, in a first aspect thereof, the present invention relates to a quaternary ammonium compound represented by general formula (I) or (I'):

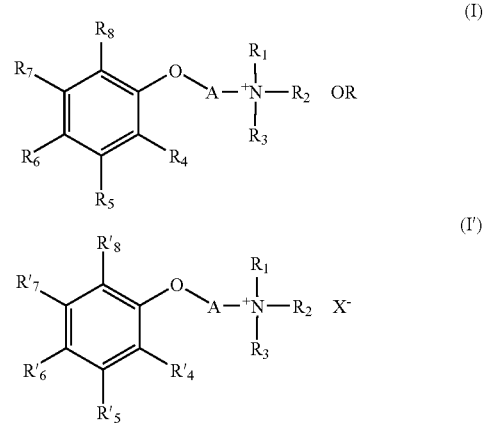

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$ to $R_3$ may be the same or different and represent a linear or branched alkyl group having 1 to 12 carbon atoms, one of $R_4$ to $R_8$ represents $CO_2^-$ or $SO_3^-$, while no more than three of the remaining $R_4$ to $R_8$ represent a group selected from the group consisting of a hydroxyl group and an alkoxy group having 1 to 4 carbon atoms, and other $R_4$ to $R_8$ represent a hydrogen atom, one of $R'_4$ to $R'_8$ represents $CO_2H$ or $SO_3H$, no more than two of the remaining $R'_4$ to $R'_8$ represent a hydroxyl group, while other $R'_4$ to $R'_8$ represent a hydrogen atom, and $X^-$ represents an anion capable of forming a salt with a quaternary ammonium group).

(2) In the aforementioned quaternary ammonium compound, one of $R_4$ to $R_8$ is preferably $CO_2^-$, or one of $R'_4$ to $R'_8$ is preferably $CO_2H$.

(3) Similarly, one of $R_4$ to $R_8$ is preferably $SO_3^-$, or one of $R'_4$ to $R'_8$ is preferably $SO_3H$.

(4) In (2) above, one of the remaining $R_4$ to $R_8$ or one of the remaining $R'_4$ to $R'_8$ is preferably a hydroxyl group.

(5) In (3) above, one of the remaining $R_4$ to $R_8$ or one of the remaining $R'_4$ to $R'_8$ is preferably a hydroxyl group.

(6) In (4) above, A is preferably a linear alkyl group having 2 carbon atoms.

(7) In (5) above, A is preferably a linear alkyl group having 2 carbon atoms.

(8) In (6) above, $R_1$ to $R_3$ are preferably methyl groups.

(9) In (7) above, $R_1$ to $R_3$ are preferably methyl groups.

(10) In a second aspect thereof, the present invention relates to a process for producing a quaternary ammonium compound represented by general formula (I):

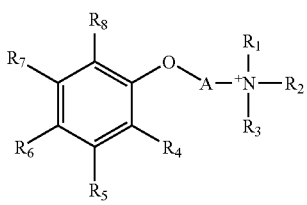

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$, $R_2$ and $R_3$ may be the same or different and represent a linear or branched alkyl group having 1 to 12 carbon atoms, one of $R_4$ to $R_8$ represents $CO_2^-$ or $SO_3^-$, while no more than three of the remaining $R_4$ to $R_8$ represent a group selected from the group consisting of a hydroxyl group and an alkoxy group having 1 to 4 carbon atoms, and other $R_4$ to $R_8$ represent a hydrogen atom) comprising: reacting with a phenol derivative represented by general formula (II):

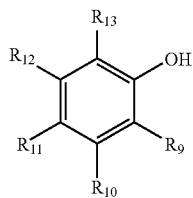

(wherein, one of $R_9$ to $R_{13}$ represents a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, and other $R_9$ to $R_{13}$ represent a hydrogen atom) a sulfonic acid ester derivative represented by general formula (III):

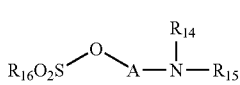

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R'_4$ to $R_{15}$ may be the same or different and represent a linear or branched alkyl group having 1 to 12 carbon atoms, and $R_{16}$ represents a lower alkyl group having 1 to 4 carbon atoms or an aryl group having 6 to 7 carbon atoms) in an organic solvent and in the presence of a basic substance, to obtain a an amino compound represented by general formula (IV):

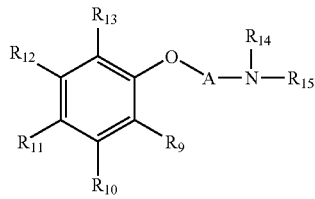

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, one of $R_9$ to $R_{13}$ represents a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, other $R_9$ to $R_{13}$ represent a hydrogen atom, and $R'_4$ to $R_{15}$ may be the same or different and represent a linear or branched alkyl group having 1 to 12 carbon atoms), and a linear or branched alkyl halide having 1 to 12 carbon atoms or a sulfonic acid ester esterified by a linear or branched alkyl group having 1 to 12 carbon atoms is reacted with a compound represented by general formula (IV), followed by deprotecting the carboxyl group or the sulfonic acid group protected by an ester group, and the protected hydroxyl group, and treating with an ion exchange resin.

(11) In a third aspect thereof, the present invention relates to a process for producing a quaternary ammonium compound represented by general formula (I'):

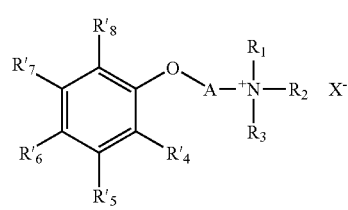

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$, $R_2$ and $R_3$ may be the same or different and represent a linear or branched alkyl group having 1 to 12 carbon atoms, one of $R'_4$ to $R'_8$ represents $CO_2H$ or $SO_3H$, while no more than three of the remaining $R'_4$ to $R'_8$ represent a group selected from the group consisting of a hydroxyl group and an alkoxy group having 1 to 4 carbon atoms, other $R'_4$ to $R'_8$ represent a hydrogen atom, and $X^-$ represents an anion capable of forming a salt with a quaternary ammonium group) comprising: reacting with a phenol derivative represented by general formula (II):

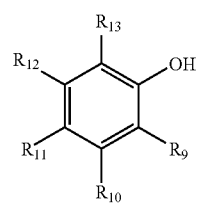

(wherein, one of $R_9$ to $R_{13}$ represents a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, and other $R_9$ to $R_{13}$ represent a hydrogen atom) a sulfonic acid ester derivative represented by general formula (III):

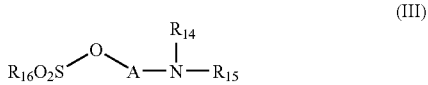

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R'_4$ to $R_{15}$ may be the same or different and represent a linear or branched alkyl group having 1 to 12 carbon atoms, and $R_{16}$ represents a lower alkyl group having 1 to 4 carbon atoms or an aryl group having 6 to 7 carbon atoms) in an organic solvent and in the presence of a basic substance, to obtain a an amino compound represented by general formula (IV):

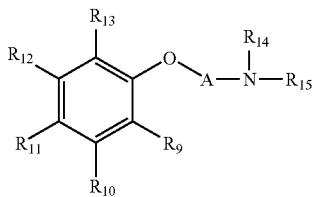

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, one of $R_9$ to $R_{13}$ represent a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, other $R_9$ to $R_{13}$ represent a hydrogen atom, and $R'_4$ to $R_{15}$ may be the same or different and represent a linear or branched alkyl group having 1 to 12 carbon atoms), and a linear or branched alkyl halide having 1 to 12 carbon atoms or a sulfonic acid ester esterified by a linear or branched alkyl group having 1 to 12 carbon atoms is reacted with a compound represented by general formula (IV), followed by de-protecting the carboxyl group or the sulfonic acid group protected by an ester group, and the protected hydroxyl group, and treating with an acidic substance.

(12) In (10) and (11) above, the organic solvent used in the step for reacting a sulfonic acid ester derivative represented by general formula (III) with a phenol derivative represented by general formula (II) is preferably an alcohol, ether or amide organic solvent.

(13) In (12) above, $R_{16}$ of general formula (III) is preferably a methyl group.

(14) In (13) above, the organic solvent used in the step for reacting a sulfonic ester derivative represented by general formula (III) with a phenol derivative represented by general formula (II) is preferably an ether organic solvent having 4 to 6 carbon atoms.

(15) In a fourth aspect thereof, the present invention relates to a therapeutic agent for cerebrovascular disorder having for an active ingredient thereof any of the quaternary ammonium compounds of (1) to (9) above.

(16) In a therapeutic agent for cerebrovascular disorder of (15) above, the cerebrovascular disorder is preferably cerebral infarction, cerebral thrombosis, cerebral embolism, transient ischemic attack or a functional disorder caused by these diseases.

(17) In a fifth aspect thereof, the present invention relates to the use of any of the quaternary ammonium compounds of (1) to (9) above.

(18) In a sixth aspect thereof, the present invention relates to a treatment method for a cerebrovascular disorder using any of the quaternary ammonium compounds of (1) to (9) above.

(19) In a seventh aspect thereof, the present invention relates to a therapeutic agent for heart disease having for an active ingredient thereof any of the quaternary ammonium compounds of (1) to (9) above.

(20) In an eighth aspect thereof, the present invention relates to the use of a any of the quaternary ammonium compounds of (1) to (9) above to produce a heart disease therapeutic agent.

(21) In a ninth aspect thereof, the present invention relates to a treatment method for a heart disease using any of the quaternary ammonium compounds of (1) to (9) above.

The present invention provides a novel quaternary ammonium compound, a therapeutic agent for cerebrovascular disorder and heart disease which demonstrate superior pharmacological efficacy by having said quaternary ammonium compound as an active ingredient thereof, and a process for producing a novel quaternary ammonium compound enabling production of said quaternary ammonium compound at high yield.

BEST MODE FOR CARRYING OUT THE INVENTION $R_1$ to $R_3$ in a quaternary ammonium compound represented by general formula (I) or (I') of the present invention:

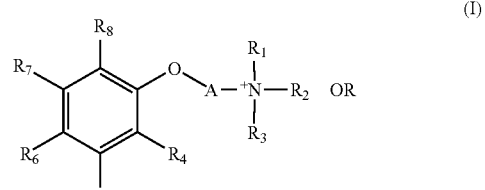

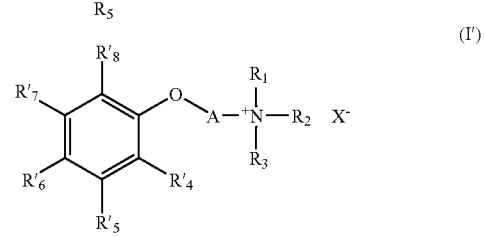

may be the same or different and represent a linear or branched alkyl group having 1 to 12 carbon atoms, more specifically an alkyl group having 1 to 12 carbon atoms such as a methyl, ethyl, propyl, isopropyl, n-butyl, s-butyl, pentyl, hexyl, octyl or dodecyl group, preferably a lower alkyl group having 1 to 4 carbon atoms, and particularly preferably a methyl group.

One of $R_4$ to $R_8$ represented in general formula (I) is $CO_2^-$ or $SO_3^-$, no more than three of the remaining $R_4$ to $R_8$ represent a group selected from a hydroxyl group and an alkoxy group having 1 to 4 carbon atoms, and other $R_4$ to $R_8$ represent a hydrogen atom. Here, although the remaining $R_4$ to $R_8$ may or may not include a hydroxyl group, they preferably include at least one hydroxyl group. In addition, one of $R'_4$ to $R'_8$ represented in general formula (I') is $CO_2H$ or $SO_3H$, no more than three of the remaining $R'_4$ to $R'_8$ represent a group selected from a hydroxyl group and an alkoxy group having 1 to 4 carbon atoms, the other $R'_4$ to $R'_8$ represent a hydrogen atom, and $X^-$ represents an anion capable of forming a salt with a quaternary ammonium group. Here, although the remaining $R'_4$ to $R'_8$ may or may not include a hydroxyl group, they preferably include at least one hydroxyl group.

A in general formula (I) represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 atoms and a hydroxyl group. Although examples of alkyl groups represented by A include linear alkyl groups such as $CH_2$, $CH_2CH_2$, $CH_2CH_2CH_2$ and $CH_2CH_2CH_2CH_2$, branched alkyl groups such as $CH(CH_3)$, $CH(CH_3)CH_2$, $CH(CH_3)CH_2CH_2$ and $CH_2CH(CH_3)CH_2$, and groups in which a hydroxyl group has been substituted into these alkyl groups, linear alkyl groups are preferable, and $CH_2CH_2$ is particularly preferable.

$X^-$ in the aforementioned general formula (I') may be any anion capable of forming a salt with an ordinary ammonium group, examples of which include halogen ions such as fluorine ion, chlorine ion, bromine ion and iodine ion, hydroxide ion, and organic ions such as formate anion, acetate anion, propionate anion, methanesulfonate anion, p-toluenesulfonate anion, oxalate anion, succinate anion, maleate anion and phthalate anion. In addition, other examples include anions of minerals such as carbonate ion, sulfate ion, nitrate ion and phosphate ion.

In addition, although the quaternary ammonium compound is optically active depending on the substituents of the carbon atoms, the optically active form included herein may be the R form or the S form.

Next, the following provides an explanation of a process for producing compounds represented by general formulas (I) and (I').

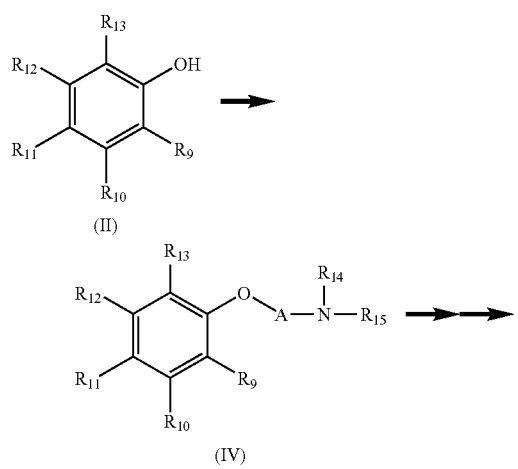

(II)

(IV)

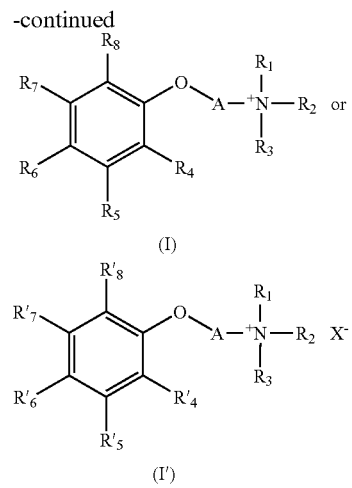

(In the formulas, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$ to $R_3$ may be the same or different and represent a linear or branched alkyl group having 1 to 12 carbon atoms, one of $R_4$ to $R_8$ represents $CO_2^-$ or $SO_3^-$, while no more than three of the remaining $R_4$ to $R_8$ represent a group selected from the group consisting of a hydroxyl group and an alkoxy group having 1 to 4 carbon atoms, and other $R_4$ to $R_8$ represent a hydrogen atom, one of $R'_4$ to $R'_8$ represents $CO_2H$ or $SO_3H$, no more than three of the remaining $R'_4$ to $R'_8$ represent a group selected from a hydroxyl group and an alkoxy group having 1 to 4 carbon atoms, while other $R'_4$ to $R'_8$ represent a hydrogen atom, and $X^-$ represents an anion capable of forming a salt with a quaternary ammonium group. In addition, one of $R_9$ to $R_{13}$ represents a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, and other $R_9$ to $R_{13}$ represent a hydrogen atom, and $R'_4$ to $R_{15}$ may be the same or different and represent a linear or branched alkyl group having 1 to 12 carbon atoms.)

First, in a first step, an alkylation reaction is carried out between a compound represented by the aforementioned general formula (II) and a sulfonic acid ester represented by general formula (III):

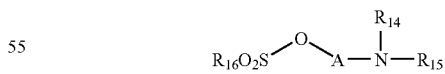

(wherein, each of the symbols in the formula are the same as previously defined). An example of a compound used for the compound represented by general formula (III) is, in the case of producing a compound in which A is $CH_2CH_2$, a sulfonic acid ester such as (2-dimethylaminoethyl)-methane sulfonate hydrochloride. Here, although examples of sulfonic acid esters include methane sulfonic acid ester, ethane sulfonic acid ester, trifluoromethane sulfonic acid ester, benzene sulfonic acid ester, toluene sulfonic acid ester and nitrotoluene sulfonic acid ester, methane sulfonic acid ester is preferable. These sulfonic acid esters can be produced according to known production methods.

The reaction is carried out in the presence of a basic substance, and substances used in ordinary alkylation reactions can be used for the basic substance used, examples of which include alkaline metals, alkaline metal hydrides, and depending on the type of compound represented by general formula (II), metal alcolates and metal hydroxides. Examples of alkaline metals include sodium and potassium, examples of alkaline metal hydrides include lithium hydride, sodium hydride and potassium hydride, examples of metal alcolates include sodium methoxide and sodium ethoxide, and examples of metal hydroxides include sodium hydroxide and potassium hydroxide.

These basic substances can normally be used at 1 to 5 times the number of moles, and preferably 1 to 3 times the number of moles, based on the reacted compound (I).

In addition, the present reaction is carried out in an organic solvent. Examples of solvents used include lower alcohols such as methanol, ethanol, propanol and isopropanol, and cyclic or linear ethers having 4 to 6 carbon atoms such as tetrahydrofuran, 1,4-dioxane, tetrahydropyran, 1,2-dimethoxyethane and bis(2-methoxyethyl)ether, with 1,2-methoxyethane being particularly preferable. In addition, an examples of amide organic solvents include N,N-dimethylformamide, N,N-dimethylacetoamide and N-methylpyrrolidone.

Although varying according to the basic substance used and type of reaction solvent, the reaction temperature is typically −20 to 120° C., and preferably 0 to 80° C., and the reaction time is normally 1 to 10 hours.

Similarly, compounds in which A is a group other than $CH_2CH_2$ can be produced using a sulfonic acid ester having a corresponding alkyl group.

Next, a quaternary ammoniumation reaction of the resulting compound (IV) is carried out in a second step.

In this reaction, ordinary reagents used to produce quaternary ammonium compounds can be used, examples of which include linear or branched alkyl halides having 1 to 12 carbon atoms such as methyl iodide, ethyl iodide, butyl bromide, isobutyl bromide, hexyl bromide, octyl bromide, decyl bromide and dodecyl bromide, and examples of halides including chlorides, bromides and iodides. In addition, examples of reagents such as sulfonic acid esters include methyl methanesulfonate, ethyl methanesulfonate, hexyl methanesulfonate, octyl methanesulfonate, decyl methanesulfonate, methyl toluenesulfonate, ethyl toluenesulfonate, octyl toluenesulfonate and dodecyl toluenesulfonate. This reaction can be carried out in an organic solvent which does not inhibit the reaction, examples of which include alcoholic solvents such as methanol, ethanol and propanol.

Although varying according to the basic substance used and type of reaction solvent, the reaction temperature is typically −20 to 120° C., and preferably 0 to 80° C., and the reaction time is normally 1 to 5 hours.

Finally, a de-protecting reaction is carried out. In the case of a carboxyl group in which $R_9$ to $R_{13}$ are protected by ester groups, the compound can be reacted with a basic substance in an organic solvent, water-containing organic solvent or water. Examples of basic substances include alkaline metal hydroxides such as sodium hydroxide and potassium hydroxide, while examples of organic solvents used include alcoholic solvents such as methanol, ethanol and propanol. In addition, in the case a hydroxyl group has a protecting group, the protecting group may be used as a protecting group as an ordinary hydroxyl group protecting group without having affect on the previous alkylation reaction, and examples of which include a methyl or other lower alkyl group and a benzyl or other aralkyl group. These de-protecting reactions can be carried out according to known methods.

Moreover, treatment using an ion exchange resin is carried out to produce a compound represented by general formula (I). An anion exchange resin is preferable for the ion exchange resin, and treatment can be carried out according to an ordinary treatment method such as by charging the resin into a cylindrical column, applying the compound after de-protecting, developing with purified water, and concentrating the fraction under reduced pressure.

In addition, a compound represented by general formula (I') can be produced by treating a compound following de-protection by adding an acidic substance in a reaction vessel. Examples of acidic substances include inorganic acids such as hydrochloric acid and hydrobromic acid, organic carboxylic acids such as formic acid, acetic acid, oxalic acid and propionic acid, and sulfonic acids such as methanesulfonic acid, toluenesulfonic acid and nitrobenzenesulfonic acid. A compound represented by general formula (I') obtained in this manner can normally be purified by recrystallization to obtain a purified product.

Moreover, a compound represented by general formula (I) or general formula (I') can also be produced in the same manner in the case in which one of $R_4$ to $R_8$ is $SO_3^-$ or one of $R'_4$ to $R'_8$ is $SO_3H$.

Specific examples of quaternary ammonium compounds represented by general formula (I) of the present invention are listed in the following Tables 1 and 2.

In the tables, Me indicates a methyl group, Et an ethyl group, Bu a butyl group, Hex a hexyl group, Oct an octyl group, Dod a dodecyl group and a blank space indicates a hydrogen atom. However, the scope of a quaternary ammonium compound as referred to in the present invention is not limited by these descriptions.

TABLE 1

| Symbol | $R_1$ | $R_2$ | $R_3$ | $R_4$ | $R_5$ | $R_6$ | $R_7$ | $R_8$ | A |
|---|---|---|---|---|---|---|---|---|---|
| 1 | Me | Me | Me | $CO_2^-$ | | | | | $CH_2CH_2$ |
| 2 | Me | Me | Me | | $CO_2^-$ | | | | $CH_2CH_2$ |
| 3 | Me | Me | Me | | | $CO_2^-$ | | | $CH_2CH_2$ |
| 4 | Me | Me | Me | $CO_2^-$ | OH | | | | $CH_2CH_2$ |
| 5 | Me | Me | Me | $CO_2^-$ | | OH | | | $CH_2CH_2$ |
| 6 | Me | Me | Me | $CO_2^-$ | | | OH | | $CH_2CH_2$ |
| 7 | Me | Me | Me | $CO_2^-$ | | | | OH | $CH_2CH_2$ |
| 8 | Me | Me | Me | OH | $CO_2^-$ | | | | $CH_2CH_2$ |
| 9 | Me | Me | Me | | $CO_2^-$ | OH | | | $CH_2CH_2$ |
| 10 | Me | Me | Me | | $CO_2^-$ | | OH | | $CH_2CH_2$ |
| 11 | Me | Me | Me | | $CO_2^-$ | | | OH | $CH_2CH_2$ |

TABLE 1-continued

| Symbol | $R_1$ | $R_2$ | $R_3$ | $R_4$ | $R_5$ | $R_6$ | $R_7$ | $R_8$ | A |
|---|---|---|---|---|---|---|---|---|---|
| 12 | Me | Me | Me | OMe | $CO_2^-$ | | | | $CH_2CH_2$ |
| 13 | Me | Me | Me | | $CO_2^-$ | OMe | | | $CH_2CH_2$ |
| 14 | Me | Me | Me | | $CO_2^-$ | | OBu | | $CH_2CH_2$ |
| 15 | Me | Me | Me | | $CO_2^-$ | | | OBu | $CH_2CH_2$ |
| 16 | Me | Me | Me | OH | | $CO_2^-$ | | | $CH_2CH_2$ |
| 17 | Me | Me | Me | | OH | $CO_2^-$ | | | $CH_2CH_2$ |
| 18 | Et | Et | Et | | | $CO_2^-$ | OH | | $CH_2CH_2$ |
| 19 | Et | Et | Et | | | $CO_2^-$ | | OH | $CH_2CH_2$ |
| 20 | Me | Me | Me | $CO_2H$ | OH | | | | $CH_2CH_2$ |
| 21 | Me | Me | Me | $CO_2H$ | | OH | | | $CH_2CH_2$ |
| 22 | Me | Me | Me | $CO_2H$ | | | OH | | $CH_2CH_2$ |
| 23 | Me | Me | Me | $CO_2H$ | | | | OH | $CH_2CH_2$ |
| 24 | Me | Me | Me | OH | $CO_2H$ | | | | $CH_2CH_2$ |
| 25 | Me | Me | Me | | $CO_2H$ | OH | | | $CH_2CH_2$ |
| 26 | Me | Me | Me | | $CO_2H$ | | OH | | $CH_2CH_2$ |
| 27 | Me | Me | Me | | $CO_2H$ | | | OH | $CH_2CH_2$ |
| 28 | Me | Me | Me | OH | $CO_2H$ | | OH | | $CH_2CH_2$ |
| 29 | Me | Me | Me | | $CO_2H$ | OH | OH | | $CH_2CH_2$ |
| 30 | Me | Me | Me | | $CO_2H$ | OH | | OH | $CH_2CH_2$ |
| 31 | Me | Me | Me | | $CO_2H$ | | OH | OH | $CH_2CH_2$ |
| 32 | Me | Me | Me | OH | OH | $CO_2H$ | | | $CH_2CH_2$ |

TABLE 2

| Symbol | $R_1$ | $R_2$ | $R_3$ | $R_4$ | $R_5$ | $R_6$ | $R_7$ | $R_8$ | A |
|---|---|---|---|---|---|---|---|---|---|
| 33 | Me | Me | Me | $CO_2H$ | OH | OH | | | $CH_2CH_2$ |
| 34 | Me | Me | Me | $CO_2H$ | OH | | OH | | $CH_2CH_2$ |
| 35 | Me | Me | Me | $CO_2H$ | OH | | | OH | $CH_2CH_2$ |
| 36 | Me | Me | Me | $CO_2H$ | | OH | OH | | $CH_2CH_2$ |
| 37 | Me | Me | Me | $CO_2H$ | | OH | | OH | $CH_2CH_2$ |
| 38 | Me | Me | Me | OMe | $CO_2H$ | | | | $CH_2CH_2$ |
| 39 | Me | Me | Me | | $CO_2H$ | | | OMe | $CH_2CH_2$ |
| 40 | Me | Me | Me | | $CO_2H$ | | OEt | | $CH_2CH_2$ |
| 41 | Me | Me | Me | | $CO_2H$ | | | OEt | $CH_2CH_2$ |
| 42 | Me | Me | Me | OH | | $CO_2H$ | | | $CH_2CH_2$ |
| 43 | Me | Me | Me | | OH | $CO_2H$ | | | $CH_2CH_2$ |
| 44 | Me | Me | Me | | OH | $CO_2H$ | OH | | $CH_2CH_2$ |
| 45 | Et | Et | Et | | | $CO_2H$ | OH | | $CH_2CH_2$ |
| 46 | Et | Et | Et | | | $CO_2H$ | | OH | $CH_2CH_2$ |
| 47 | Me | Me | Me | | $CO_2^-$ | | OH | OH | $CH_2CH_2$ |
| 48 | Me | Me | Bu | $CO_2^-$ | | | | | $CH_2CH_2$ |
| 49 | Me | Me | Oct | | $CO_2^-$ | | | | $CH_2CH_2$ |
| 50 | Me | Me | Dod | | | $CO_2^-$ | | | $CH_2CH_2$ |
| 51 | Me | Me | Me | | $CO_2H$ | | | OH | $CH_2$ |
| 52 | Me | Me | Me | | $CO_2H$ | | | OH | $CH_2CH_2CH_2$ |
| 53 | Me | Me | Me | | $CO_2H$ | | | OH | $CH_2CH_2CH_2CH_2$ |
| 54 | Me | Me | Me | | $CO_2H$ | | | OH | $CH(CH_3)CH_2$ |
| 55 | Me | Me | Me | | $CO_2H$ | OH | | | $CH_2CH(CH_3)CH_2$ |
| 56 | Me | Me | Me | | $CO_2H$ | OH | | | $CH(OH)CH_2$ |
| 57 | Me | Me | Me | | $CO_2H$ | OH | | | $CH_2CH(OH)CH_2$ |
| 58 | Me | Me | Me | $SO_3^-$ | | | | | $CH_2CH_2$ |
| 59 | Me | Me | Me | | $SO_3^-$ | | | | $CH_2CH_2$ |
| 60 | Me | Me | Me | | | $SO_3^-$ | | | $CH_2CH_2$ |
| 61 | Me | Me | Me | $SO_3H$ | OH | | | | $CH_2CH_2$ |
| 62 | Me | Me | Me | $SO_3H$ | | OH | | | $CH_2CH_2$ |
| 63 | Me | Me | Me | $SO_3H$ | | | OH | | $CH_2CH_2$ |
| 64 | Me | Me | Me | $SO_3H$ | | | | OH | $CH_2CH_2$ |

TABLE 3

| Symbol | $R_1$ | $R_2$ | $R_3$ | $R_4$ | $R_5$ | $R_6$ | $R_7$ | $R_8$ | A |
|---|---|---|---|---|---|---|---|---|---|
| 65 | Me | Me | Me | OH | $SO_3H$ | | | | $CH_2CH_2$ |
| 66 | Me | Me | Me | | $SO_3H$ | OH | | | $CH_2CH_2$ |
| 67 | Me | Me | Me | | $SO_3H$ | | OH | | $CH_2CH_2$ |
| 68 | Me | Me | Me | | $SO_3H$ | | | OH | $CH_2CH_2$ |
| 69 | Me | Me | Me | OH | | $SO_3H$ | | | $CH_2CH_2$ |
| 70 | Me | Me | Me | | OH | $SO_3H$ | | | $CH_2CH_2$ |
| 71 | Et | Et | Et | | | $SO_3H$ | OH | | $CH_2CH_2$ |
| 72 | Et | Et | Et | | | $SO_3H$ | | OH | $CH_2CH_2$ |
| 73 | Me | Me | Et | $SO_3^-$ | | | | | $CH_2CH_2$ |

TABLE 3-continued

| Symbol | $R_1$ | $R_2$ | $R_3$ | $R_4$ | $R_5$ | $R_6$ | $R_7$ | $R_8$ | A |
|---|---|---|---|---|---|---|---|---|---|
| 74 | Me | Me | Bu | | $SO_3^-$ | | | | $CH_2CH_2$ |
| 75 | Me | Me | Hex | | | $SO_3^-$ | | | $CH_2CH_2$ |
| 76 | Me | Me | Me | | $SO_3^-$ | | | OH | $CH_2$ |
| 77 | Me | Me | Me | | $SO_3^-$ | | | OH | $CH_2CH_2CH_2$ |
| 78 | Me | Me | Me | | $SO_3^-$ | | | OH | $CH_2CH_2CH_2CH_2$ |
| 79 | Me | Me | Me | | $SO_3^-$ | | OH | OH | $CH_2CH_2$ |

A quaternary ammonium compound referred to in the present invention may be a compound represented by general formula (I), namely a compound which forms a salt within a molecule thereof, or a compound which forms a salt with a physiologically acceptable anion between molecules of a compound represented by general formula (I').

A quaternary ammonium compound of the present invention can be used as an extremely superior therapeutic agent for cerebrovascular disorder. A cerebrovascular disorder as referred to in the present invention indicates a state presenting with any form of neurological or psychological symptoms caused by the occurrence of a circulatory disorder in the brain, and includes functional disorders caused by cerebral infarction, cerebral thrombosis, cerebral embolism, transient ischemic attack and diseases thereof. According to the Ministry of Health, Labor and Welfare, cerebrovascular disorder was the third highest cause of death among Japanese in 2002, and the total number of patients suffering from such diseases reached 1.7 million, thus creating a strong need for a pharmaceutical having therapeutic effects on this disorder.

An administration method ordinarily used for the administration of pharmaceuticals may be used in the case of using a compound of the present invention for the treatment of cerebrovascular disorder, and oral or parenteral administration may be used. An example of a preferable administration method is intravenous administration.

Although varying corresponding to the drug form, the content of a compound of the present invention in such a preparation is typically preferably 0.01 to 100% by weight.

Although the dose of a compound of the present invention can be varied over a wide range according to, for example, the type of target mammal such as a human, the severity of the symptoms and the discretion of a physician, in the case of oral administration, the dose is preferably 0.01 to 50 mg/day/kg of body weight, and particularly preferably 0.05 to 10 mg/day/kg of body weight. In addition, the dose in the case of parenteral administration is similarly preferably 0.01 to 10 mg/day/kg of body weight. In addition, the aforementioned doses may be administered once a day or divided among several administrations, and can be suitably adjusted corresponding to the severity of patient symptoms, discretion of a physician and so forth.

In addition, a quaternary ammonium compound of the present invention can be used as an extremely superior therapeutic agent for heart disease. Heart disease as referred to in the present invention indicates arrhythmias such as supraventricular extrasystole, paroxysmal supraventricular tachycardia, paroxysmal atrial fibrillation, chronic atrial fibrillation, atrial fibrillation, ventricular extrasystole, ventricular tachycardia, ventricular fibrillation and atrial block, arrhythmia accompanying ischemic heart disease (such as myocardial infarction and angina pectoris), acute myocardial infarction, chronic myocardial infarction, cardiac insufficiency, angina pectoris and Wolff-Parkinson-White (WPW) syndrome.

An administration method ordinarily used for the administration of pharmaceuticals may be used in the case of using a compound of the present invention for the treatment of heart disease, and oral or parenteral administration may be used. An example of a preferable administration method is intravenous administration using an injection preparation.

Although varying corresponding to the drug form, the content of a compound of the present invention in such a preparation is typically preferably 0.01 to 100% by weight. The dose of a compound of the present invention in this case is the same as in the case of treatment of cerebrovascular disease.

Although the following provides a detailed explanation of the present invention through its examples and reference examples, the scope of the present invention is naturally not limited by the scope of these examples.

Comparative Example 1

Ethyl 4-(2-dimethylaminoethoxy) Benzoate
(Aforementioned Production Process of M. B.
Moore, J. Amer. Chem. Soc., 78:5633-5636 (1956))

1.66 g of ethyl 4-hydroxybenzoate (10 mmol) were added to 6 mL of ethanol in a nitrogen atmosphere followed by the addition of 0.68 g (10 mmol) of sodium ethoxide. On the other hand, 1.51 g (10.5 mmol) of (2-chloroethyl)-dimethylamine hydrochloride were dissolved in 10 mL of water followed by the addition of 0.42 g (10.5 mmol) of sodium hydroxide and extraction of (2-chloroethyl)-dimethylamine with hexane. Next, the hexane solution was added to the ethanol reaction solution and allowed to react for 1.5 hours while distilling off the hexane by heating and refluxing. After acidifying the reaction solution by addition of 5% sulfuric acid, the solvent was distilled off under reduced pressure and the resulting precipitate was filtered. After washing the filtrate with ethyl acetate, the aqueous layer was basified with aqueous sodium bicarbonate and extracted with ethyl acetate. The ethyl acetate solution was then dried with magnesium sulfate followed by distilling off the solvent under reduced pressure to obtain 0.57 g of the target substance (yield: 23%).

1H-NMR (300 MHz, CDCL3): δ=7.98 (d, 2H, J=9.0 Hz), 6.93 (d, 2H, J=9.0 Hz), 4.34 (q, 2H, J=7.1 Hz), 4.11 (t, 2H, J=5.7 Hz), 2.74 (t, 2H, J=5.7 Hz), 2.33 (s, 6H), 1.38 (t, 2H, J=7.1 Hz)

13C-NMR (75.5 MHz, CDCl$_3$): δ=166.40, 162.56, 131.52, 123.04, 114.14, 66.25, 60.62, 58.18, 45.95, 14.39

Comparative Example 2

Ethyl 3-(2-dimethylaminoethoxy)-4-methoxy
Benzoate 10.0 g (51.0 mmol) of ethyl 3-hydroxy-4-methoxybenzoate and 100 mL of N,N-dimethylformamide were placed in a 300 mL three-mouth flask and dissolved by stirring. 5.7 g (143 mmol) of sodium hydride (60 wt %) were added to this solution while cooling, and after the foaming had subsided, 11.0 g (76.4 mmol) of (2-chloroethyl)-dimethylammonium chloride were added followed by heating and stirring after again waiting until the foaming had subsided. After stirring for 4 hours at about 50° C., the reaction solution was cooled followed by the addition of the reaction solution to 1 mol/L hydrochloric acid containing ice to bring the pH of the liquid to 1 followed by washing with ethyl acetate. Sodium bicarbonate was added to the resulting aqueous layer to adjust the pH to 8 followed by extracting with ethyl acetate and drying the organic layer with magnesium sulfate. After filtering the drying agent, the filtrate was concentrated under reduced pressure to obtain 3.4 g of the target substance (yield: 25%).

1H-NMR (300 MHz, CDCl$_3$): δ=7.68 (dd, 1H, J=2.0, 8.4 Hz), 7.58 (d, 1H, J=2.0 Hz), 6.88 (d, 1H, J=8.4 Hz), 4.35 (q, 2H, J=7.1 Hz), 4.16 (t, 2H, J=6.0 Hz), 3.90 (s, 3H), 2.80 (t, 2H, J=6.0 Hz), 2.35 (s, 6H), 1.38 (t, 3H, J=7.1 Hz)

13C-NMR (300 MHz, CDCl$_3$): δ=166.29, 153.36, 147.85, 123.71, 122.91, 113.88, 110.49, 67.14, 60.67, 58.03, 55.87, 45.91, 14.32

IR (KBr): ν=2941, 1713, 1601, 1515, 1428, 1291, 1271, 1219, 1133, 1027, 765 cm$^{-1}$

Example 1

[2-(4-ethoxycarbonyl-phenoxy)-ethyl]-trimethylammonium p-toluenesulfonate 25.0 g (0.11 mol) of the ethyl 4-(2-dimethylaminoethoxy) benzoate obtained in Comparative Example 1 were dissolved in 250 mL of methanol in a nitrogen atmosphere. After adding 23.6 g (0.13 mol) of methyl p-toluenesulfonate while stirring at room temperature, the solution was stirred for 2 hours while heating to 50° C. After distilling off the solvent, the resulting residue was recrystallized from a mixed solvent of 100 mL of methanol and 500 mL of ethyl acetate to obtain 35.9 g of the target substance (yield: 81%).

1H-NMR (300 MHz, DMSO-d6): δ=7.95 (d, 2H, J=6.6 Hz), 7.49 (d, 2H, J=6.3 Hz), 7.10 (m, 4H), 4.54 (m, 2H), 4.29 (q, 2H, J=5.1 Hz), 3.82 (m, 2H), 3.19 (s, 9H), 2.29 (s, 3H), 1.31 (t, 2H, J=5.1 Hz)

13C-NMR (75.7 MHz, DMSO-d6): δ=165.21, 161.08, 145.73, 137.46, 131.07, 127.93, 125.41, 122.84, 114.62, 63.92, 61.82, 60.32, 53.05, 20.69, 14.13

Example 2

Ethyl 3-hydroxy-4-methoxybenzoate 20.0 g (0.12 mol) of 3-hydroxy-4-methoxybenzoate and 200 mL of tetrahydrofuran were placed in 500 mL four-mouth flask and dissolved. 80 mL (0.57 mol) of triethylamine were added to this solution at room temperature followed by adding 40 mL (0.31 mol) of diethyl sulfate and stirring while heating. After stirring up for 1 hour at 60° C., the reaction mixture was poured into water and the pH was adjusted to 7 with 1 mol/L hydrochloric acid followed by extraction with ethyl acetate. The resulting organic layer was dried with magnesium sulfate followed by filtering out the drying agent and concentrating under reduced pressure. The resulting residue was purified with a silica gel column chromatograph using for the elution solvent a 1:4 mixture of acetone and hexane to obtain 21.1 g of the target substance (yield: 90%).

1H-NMR (300 MHz, CDCl$_3$): δ=7.62 (m, 2H), 6.86 (d, 1H, J=8.6 Hz), 5.76 (s, 1H), 4.34 (q, 2H, J=7.1 Hz), 3.93 (s, 3H), 1.37 (t, 3H, J=7.1 Hz)

13C-NMR (75.5 MHz, CDCl$_3$): δ=166.33, 150.33, 145.18, 123.69, 122.67, 115.56, 109.79, 60.72, 55.96, 14.29

IR (KBr): ν=3356, 2988, 1693, 1613, 1588, 1515, 1374, 1307, 1280, 1215, 1127, 1023, 764 cm$^{-1}$

Example 3

Ethyl 3-(2-dimethylaminoethoxy)-4-hydroxy-benzoate Hydrochloride 2.67 g (10 mmol) of the ethyl 3-(2-dimethylaminoethoxy)-4-methoxy-benzoate obtained in Comparative Example 2 were dissolved in 53 mL of methylene chloride and cooled to about −80° C. 12 mL (12 mmol) of boron tribromide (1 mol/L methylene chloride solution) were dropped in. The solution was returned to room temperature and allowed to stand overnight. After cooling in a salt/ice bath, 20 mL of water were added followed by neutralizing with 1 mol/L sodium hydroxide. After separating, the organic layer was dried with magnesium sulfate and concentrated. 4 mL of 20% hydrogen chloride-ethanol solution were added to the residue followed by filtering the precipitated crystals and drying to obtain 1.74 g of the target substance (yield: 60%).

1H-NMR (400 MHz, CD3OD): δ=7.69 (s, 1H), 7.68 (d, 1H, J=8.8 Hz), 6.98 (d, 1H, J=8.8 Hz), 4.46 (t, 2H, J=5.0 Hz), 4.37 Hz), 3.68 (t, 2H, J=5.2 Hz), 3.07 (s, 6H), 1.41 (t)

13C-NMR (100 MHz, CD3OD): δ=165.89, 151.11, 144.87, 124.51, 121.40, 114.78, 62.39, 60.08, 55.87, 41.85, 12.75

IR (KBr): ν=3218, 2968, 2700, 1700, 1607, 1523, 1437, 1300, 1213, 1117, 759 cm$^{-1}$

Example 4

[2-(5-ethoxycarbonyl-2-hydroxy-phenoxy)-ethyl]-trimethylammonium Chloride 1.08 g (3.73 mmol) of the ethyl 3-(2-dimethylaminoethoxy)-4-hydroxy-benzoate hydrochloride obtained in Example 3 were suspended in ethyl acetate, and after neutralizing with 1 mol/L sodium hydroxide, the liquid was separated and the organic layer was dried with magnesium sulfate followed by filtering out the drying agent and concentrating under reduced pressure. The residue was dissolved in 20 mL of methanol followed by the addition of 0.64 g (4.51 mmol) of methyl iodide and 0.37 g (3.70 mmol) of potassium hydrogen carbonate and heating to 60° C. in an oil bath. After heating and stirring for 3 hours, the solution was cooled and filtered. The filtrate was concentrated, and after adding water to dissolve the residue, the solution was neutralized with 1 mol/L hydrochloric acid followed by purification with an ion exchange chromatograph. The fraction containing the target substance was collected and concentrated followed by drying, desalting by extracting with methanol and recrystallizing from ethyl acetate to obtain 0.68 g of the target substance (yield: 60%).

1H-NMR (400 MHz, D$_2$O): δ=7.48 (d, 1H, J=8.4 Hz), 7.43 (s, 1H), 6.82 (d, 1H, J=8.4 Hz), 4.41 (br, 2H), 4.19 (q, 2H, J=7.3 Hz), 3.73 (br, 2H), 3.14 (s, 9H), 1.22 (t, 3H, J=7.2 Hz)

13C-NMR (100 MHz, D$_2$O): δ=170.45, 153.55, 147.34, 127.25, 123.19, 117.97, 116.74, 66.94, 64.74, 64.00, 55.90, 15.42

IR (KBr): ν=3408, 1704, 1516, 1291, 1218, 1108, 1024, 975, 765 cm$^{-1}$

Example 5

Sodium 4-(2-dimethylaminoethoxy)-benzenesulfonate 7.00 g (42.4 mmol) of dimethyl-(2-phenoxyethyl)-amine were dissolved in 35 mL of glacial acetic acid and cooled in an ice bath. 9.63 g (93.3 mmol) of 95% sulfuric acid were dropped in while maintaining an internal temperature of 10° C. or lower followed by stirring for 1 hour at room temperature. The solution was concentrated followed by the gradual addition of the concentrated residue to 1 mol/L sodium hydroxide to bring pH10, after which the solution was concentrated and dried. After extracting the residue with methanol, concentrating and drying, the residue was suspended in 100 mL of ethanol followed by cooling and filtration. The filtrate was concentrated and the precipitated crystals were filtered to obtain 8.36 g of the target substance (yield: 74%).

1H-NMR (400 MHz, $D_2O$): δ=7.68 (d, 2H, J=8.8 Hz), 7.01 (d, 2H, J=8.8 Hz), 4.33 (t, 2H, J=5.0 Hz), 3.53 (t, 2H, J=5.2 Hz)

13C-NMR (400 MHz, $D_2O$): δ=158.12, 133.61, 125.61, 112.90, 61.79, 54.66, 41.70

IR (KBr): ν=3431, 3097, 2770, 1599, 1180, 1032, 844 $cm^{-1}$

Example 6

Ethyl 4-(2-dimethylaminoethoxy)-benzoate (Equivalent compound of General Formula (IV))

20 g (0.12 mol) of ethyl 4-hydroxybenzoate were dissolved in 300 mL of ethylene glycol dimethyl ether in a nitrogen atmosphere. 11.6 g (0.29 mol) of 60% sodium hydroxide were added in portions over the course of 25 minutes while stirring at room temperature followed by heating to 50° C. and stirring for 1 hour. Moreover, 29.4 g (0.14 mol) of [2-(methanesulfonyloxy)ethyl]dimethylammonium chloride were added in portions over the course of 1 hour at the same temperature followed by additionally stirring for 2 hours. After adding 4 mL of acetic acid while cooling with ice, the precipitate that formed was filtered out. The filtrate was concentrated and ethyl acetate was added to the residue followed by extraction with 3% sulfuric acid. After washing the aqueous phase with ethyl acetate, potassium hydrogen carbonate was added to bring to pH8 followed by extraction with ethyl acetate. The organic layer was dried with magnesium sulfate followed by distilling off the solvent to obtain 26.3 g of the target substance (yield: 92%).

In comparison with the yield of 23% in Comparative Example 1, this yield of 92% was confirmed to represent a considerable improvement in yield.

Example 7

Ethyl 3-(2-dimethylaminoethoxy)-4-methoxy-benzoate (Equivalent compound of General Formula (IV))

The target substance was obtained in the same manner as Example 1 with the exception of using ethyl 3-hydroxy-4-methoxybenzoate instead of ethyl 4-hydroxybenzoate (yield: 94%).

In comparison with the yield of 25% in Comparative Example 2, this yield of 94% was confirmed to represent a considerable improvement in yield.

Example 8

4-(2-trimethylammonio-ethoxy)-benzoate (Compound 3)

5.5 g (0.013 mol) of the [2-(4-ethoxycarbonyl-phenoxy)-ethyl]-trimethylammonium p-toluenesulfonate obtained in Example 1 were added to 150 mL of water followed by the addition of 13 mL of 1 mol/L aqueous sodium hydroxide solution while stirring at room temperature and stirring for 6 hours. The reaction mixture was concentrated and the residue was dissolved in water followed by separating with an anion exchange column (Amberlite (trade name) type IRA402BLCL). The fraction containing the target substance was concentrated and 1.91 g of the resulting residue were recrystallized from a mixed solvent consisting of 3 mL of methanol and 10 mL of ethyl acetate to obtain 1.56 g of the target substance (yield: 54%).

1H-NMR (300 MHz, DMSO-d6/$D_2O$=8:1): δ=7.85 (d, 2H, J=8.6 Hz), 6.91 (d, 2H, J=8.6 Hz), 4.43 (m, 2H), 3.78 (m, 2H), 3.19 (s, 9H)

13C-NMR (75.5 MHz, DMSO-d6/$D_2O$=8:1): δ=171.14, 158.90, 133.20, 131.49, 113.94, 65.04, 62.23, 54.14

IR (KBr): ν=3437, 1606, 1549, 1382, 1249, 1175, 962, 792 $cm^{-1}$

Example 9

[2-(5-carboxy-2-hydroxy-phenoxy)-ethyl]-trimethylammonium Chloride (Compound 27)

9 mL (9 mmol) of 1 mol/L sodium hydroxide were added to 0.68 g (2.24 mmol) of the [2-(5-ethoxycarbonyl-2-hydroxy-phenoxy)-ethyl]-trimethylammonium chloride obtained in Example 4 followed by degassing and replacement with argon. After stirring for 1 hour at room temperature, the pH was brought to 1 with 1 mol/L hydrochloric acid followed by concentration and drying to a solid. The residue was extracted with methanol and then dried to a solid followed by removal of sodium chloride and recrystallization from ethanol to obtain 0.52 g of the target substance (yield: 85%).

1H-NMR (400 MHz, $D_2O$): δ=7.58 (dd, 1H, J=2.0, 8.0 Hz), 7.52 (d, 1H, J=2.0 Hz), 6.97 (d, 1H, J=8.0 Hz), 4.55 (br, 2H), 3.91 (t, 2H, J=4.8 Hz), 3.33 (s, 9H)

13C-NMR (100 MHz, $D_2O$): δ=170.63, 151.38, 145.87, 126.30, 122.47, 116.57, 115.89, 65.83, 63.63, 54.84

IR (KBr): ν=3451, 3017, 1673, 1598, 1518, 1449, 1311, 1231, 1193, 980, 765 $cm^{-1}$

Example 10

4-(2-trimethylammonio-ethoxy)-benzenesulfonate (Compound 59)

3.43 g (12.8 mmol) of the sodium 4-(2-dimethylaminoethoxy)-benzenesulfonate obtained in Example 5 were added to 50 mL of methanol followed by the addition of 1.98 g (18.7 mmol) of sodium carbonate and 3.18 g (22.4 mmol) of methyl iodide, heating to 60° C. in an oil bath and stirring for 1 hour. After cooling, the mixture was concentrated and 50 mL of water were added to the residue, insoluble matter was removed and the filtrate was concentrated followed by ion exchange chromatography (Amberlite (trade name) type IRA400JCL, mobile phase: water) and recrystallizing from 30% water-containing ethanol to obtain 2.85 g of a monohydrate of the target substance (yield: 80%).

1H-NMR (400 MHz, D$_2$O): δ=7.63 (d, 2H, J=9.2 Hz), 6.95 (d, 2H, J=9.2 Hz), 4.37 (m, 2H), 3.68 (t, 2H, J=4.6 Hz)

13C-NMR (400 MHz, D$_2$O): δ=160.06, 136.70, 128.29, 115.57, 65.82, 62.76, 54.88, 54.83, 54.79

IR (KBr): ν=3469, 1638, 1459 cm$^{-1}$

Example 11

[2-(4-carboxy-2-hydroxyphenoxy)-ethyl]-trimethylammonium Chloride (Compound 42)

The above compound was obtained in the same method as Example 9 with the exception of using [2-(4-ethoxycarbonyl-2-hydroxy-phenoxy)-ethyl]-trimethylammonium chloride instead of [2-(5-ethoxycarbonyl-2-hydroxy-phenoxy)-ethyl]-trimethylammonium chloride.

1H-NMR (400 MHz, D$_2$O): δ=7.43 (dd, 1H, J=2.0, 8.6 Hz), 7.32 (d, 1H, J=2.4 Hz), 6.92 (d, 1H, J=8.4 Hz), 4.46 (br, 2H), 3.75 (t, 2H, J=4.4 Hz), 3.15 (s, 9H)

13C-NMR (100 MHz, D$_2$O): δ=216.60, 165.91, 146.02, 140.76, 119.53, 112.93, 108.79, 58.55, 50.00

IR (KBr): ν=3397, 3019, 1678, 1460, 1311, 1220, 971 cm$^{-1}$

Example 12

[2-(4-carboxy-3-hydroxyphenoxy)-ethyl]-trimethylammonium chloride (Compound 43)

The above compound was obtained in the same method as Example 9 with the exception of using [2-(4-ethoxycarbonyl-3-hydroxy-phenoxy)-ethyl]-trimethylammonium chloride instead of [2-(5-ethoxycarbonyl-2-hydroxy-phenoxy)-ethyl]-trimethylammonium chloride.

1H-NMR (400 MHz, D$_2$O): δ=7.69 (d, 1H, J=6.6 Hz), 6.42 (dd, 1H, J=1.8, 6.0 Hz), 6.31 (d, 1H, J=1.8 Hz), 4.36 (br, 2H), 3.74 (t, 2H, J=3.3 Hz), 3.23 (s, 9H)

13C-NMR (75 MHz, D$_2$O): δ=175.83, 162.27, 162.01, 132.65, 112.83, 106.98, 102.04, 65.77, 62.45, 54.79

IR (KBr): ν=3401, 1593, 1443, 1377, 1262, 1165 cm$^{-1}$

Example 13

[3-(5-carboxy-2-hydroxy-phenoxy)-propyl]-trimethylammonium Chloride (Compound 52)

The above compound was obtained in the same method as Example 9 with the exception of using [3-(5-ethoxycarbonyl-2-hydroxy-phenoxy)-propyl]-trimethylammonium chloride instead of [2-(5-ethoxycarbonyl-2-hydroxy-phenoxy)-ethyl]-trimethylammonium chloride.

1H-NMR (400 MHz, D$_2$O): δ=7.50 (m, 2H), 6.83 (d, 1H, J=2.5 Hz), 3.94 (t, 2H, J=7.2 Hz), 3.30 (s, 9H), 3.24 (t, 2H, J=4.8 Hz), 2.15 (m, 2H)

13C-NMR (100 MHz, D$_2$O): δ=172.01, 148.20, 145.90, 123.80, 123.15, 117.22, 116.22, 71.10, 64.50, 49.70, 23.40

IR (KBr): ν=3445, 3017, 1667, 1518, 1225, 1193, 970, 765 cm$^{-1}$

Example 13

Safety Test

In order to investigate the safety of Compounds 3, 9, 27-33, 39, 56, 60, 66, 71 and 77 of the present invention, those compounds were intravenously administered into rats. None of the animals died following administration of any of the compounds at dose of 150 mg/kg, thereby it was demonstrated that the compounds of the present invention were superior safety.

Example 14

Efficacy Confirmation Study of Compounds of the Present Invention

In this example, a cerebral infarction model was prepared using rats in which reperfusion injury was induced by ischemia and then reperfusion of the middle cerebral artery using the obturator method. The efficacy of compounds of the present invention following single-dose intravenous administration at dose of 3 mg/kg was evaluated in terms of infarct area, neurological symptoms and motor function.

1. Materials and Methods

1) Compounds

Compounds 3, 9, 27-33, 39, 56, 60, 66, 71 and 77 of the present invention were used. In addition, Edaravone (trade name, Mitsubishi Pharma Corporation) was used as a reference compound. The compounds of the present invention were stored in a refrigerator under protection from light, while Edaravone (trade name) was stored at room temperature under protection from light.

2) Solvent

Physiological saline (Otsuka Pharmaceutical Factory, Inc.) was used for the solvent.

3) Method for Preparing Test Solution and Preparation Frequency

Compounds of present invention: 2 mL of physiological saline was added directly to tube containing 3 mg aliquots of a compound of the present invention to dissolve and prepare solutions having a concentration of 3 mg/2 mL. These samples were prepared at the time of use.

Edaravone: Since Edaravone is an injectable solution having a concentration of 30 mg/20 mL, the required amounts were divided up and used.

2. Animals and Conditions

1) Animals

Rats: Crj: Wistar strain, males, age 7 weeks (Charles River Laboratories Japan, Inc.)

Quarantine and acclimation: The animals were housed for at least 5 days following their receipt as a quarantine and acclimation period, during which time the animals were examined or general condition and weighed. Only those animals judged to be normal were used in the study.

3. Study Method

1) Administration Method

The test compounds were administered in a single dose into the tail vein using a 1 mL syringe and 27 G injection needle immediately before the reperfusion.

2) Preparation of Middle Cerebral Artery Occlusion and Reperfusion Model

The rats were anesthetized by intraperitoneal administration of sodium pentobarbital at dose of 40 mg/kg (Nembutal (trade name), Dainippon Pharmaceutical Co., Ltd.), and a middle cerebral artery occlusion and reperfusion model was prepared in accordance with the method of Koizumi et al. (Non-Patent Document 2). Namely, the animals were warmed to 37° C. and held in the dorsal position while breathing spontaneously. A midline cervical incision was made, and then the right external carotid artery and right internal carotid artery were separated without damaging the vagus nerve. The right common carotid artery and right external carotid artery were ligated, and a suture was attached to the origin of the internal carotid artery in preparation for ligation and maintenance of occlusion following insertion of an obturator into the internal carotid artery. Moreover, a small incision was made in the right common carotid artery, an obturator provided with an approximately 17 mm silicon-coated suture was inserted into the internal carotid artery, and the internal carotid artery was ligated. Two hours after ligation, the obturator was removed under unanesthesia to reperfuse. Furthermore, flexion of the contralateral forelimb was confirmed 30 minutes after occlusion of the middle cerebral artery.

3) Evaluation of Neurological Symptoms

The following neurological symptoms were evaluated 24 hours after occlusion of the middle cerebral artery according to the evaluation method of Petullo et al. (Non-Patent Document 3). Neurological symptoms consisted of flexion of the forelimbs, torso twisting, resistance when pushing on the back of the right or left shoulder (Lateral push), circling, return of the hindlimb to the floor when lifted from the floor (Hindlimb placement), behavior when the head is faced downward on an angle (Inverted angle board) and a locomotor activity test. These symptoms were observed in the manner described below.

Flexion of the forelimbs: flexion of the forelimbs was observed when the animals were lifted up by the tail.

Torso twisting: Torso twisting was observed when the animals were lifted up by the tail.

Circling: The animals were observed for the presence of circling movement.

Lateral push: Resistance was observed when pushing on the back of the right or left shoulder.

Hindlimb placement: The animals were observed as to whether or not the hindlimb immediately returns to the floor after being lifted from the floor when placed on a horizontal floor.

Inverted angle board: The animals were observed for behavior when the head was faced downward when placed on an angled board tilted at an angle of 30°.

locomotor activity: locomotor activity was observed when the animals were placed in a polycarbonate cage.

The aforementioned tests were scored based on the criteria described in the following documents, followed by calculation of total scores (see Table 4 "Neurological Symptom Evaluation Criteria and Scores").

(Document 1) Koizumi, J., Yoshida, Y., Nakazawa, S, and Oneda, G.: Experimental Research on Ischemic Cerebral Edema, Method 1, Cerebral Infarction Model Enabling Restoration of Blood Flow Using Rats, Stroke 8, 1-8, 1986.

(Document 2) Petullo, D., Masonic, C., Lincoln, C., Wibberley, L., Teliska, M. and Yao, D. L.: Model development and behavioral assessment of focal cerebral ischemia in rats, Life Science 64, 1099-1108, 1999.

TABLE 4

| Neurological Symptom Evaluation Criteria | Score | Explanation |
| --- | --- | --- |
| Flexion forelimb | 0.0 | No flexion |
|  | 0.5 | Slight flexion |
|  | 1.0 | Moderate to severe flexion |
| Torso twisting | 0.0 | No symptoms |
|  | 0.5 | Mild twisting |
|  | 1.0 | Moderate to severe twisting |

TABLE 4-continued

| Neurological Symptom Evaluation Criteria | Score | Explanation |
| --- | --- | --- |
| Lateral push | 0.0 | Equal resistance |
|  | 0.5 | Weak resistance |
|  | 1.0 | No resistance |
| Circling | 0.0 | No symptoms |
|  | 0.5 | Mild circling |
|  | 1.0 | Moderate to severe circling |
| Hindlimb placement | 0.0 | Returns immediately |
|  | 0.5 | Returns after some time |
|  | 1.0 | Does not return |
| Inverted angle board | 0.0 | Walks up after turning around 180° |
|  | 0.5 | Stops but cannot walk up |
|  | 1.0 | Tries to stop, but cannot walk up and eventually slides down |
|  | 1.5 | Tries to stop, but cannot walk up and immediately slides down |
|  | 2.0 | Unable to maintain position and slides to the bottom |
| locomotor activity | 0.0 | Normal |
|  | 1.0 | Decreased locomotor activity |
|  | 1.5 | Requires stimulus to move |
|  | 2.0 | Unable to move |

4) Evaluation of Motor Function

The time the animals were able to stay on a rotor rod set to rotate at the rate of 14 times per minute (ENV-576, Med Associates Inc.) was measured and evaluated following observation of neurological symptoms. The time was measured three times, and the longest time the animals were able to stay on the rotor rod was used for the data. In addition, the animals were observed for a maximum of 1 minute per attempt.

5) Measurement of Infarct Area ($mm^2$)

Following evaluation of neurological symptoms and motor function (measurement time: approx. 10 minutes), the animals were exsanguinated under ether anesthesia followed by isolation of the brain. Six 2-mm coronal slices of the cerebrum were prepared from the boundary between the cerebrum and cerebellum, and after staining with 1% TTC (2,3,5-triphenyltetrazolium chloride, Wako Pure Chemical Industries), photographs were taken with a digital camera followed by determination of the brain area and infarct area for the forehead side of each of the six slices using image analysis software (Image Tool Ver. 2.00, UTHSCSA), and determination of the percentage (%) of the total infarct area to the total brain area.

Evaluations were made based on calculations made using the following equation.

Rate of reduction of cerebral infarction(%)=[percentage(%) of cerebral infarct area of control group (physiological saline dose group)−percentage (%) of cerebral infarct area of compound dose group]/percentage (%) of cerebral infarcted surface area of control group (physiological saline dose group)×100(%)

Table 5 shows the average values for groups of 10 animals each for cerebral infarction reduction rate, improvement of neurological symptoms and improvement of motor function. Furthermore, smaller values indicate greater effects in neurological symptom, and bigger values indicate greater effects in infarct area and motor function.

TABLE 5

| Compound | Cerebral infarction reduction rate (%) | Improvement of neurological symptoms* | Improvement of motor function (time stayed on rotor rod: seconds) |
|---|---|---|---|
| 3 | 48.7 | 6.20 | 50.1 |
| 9 | 51.5 | 5.95 | 51.6 |
| 27 | 53.7 | 6.75 | 47.5 |
| 28 | 54.7 | 5.85 | 53.1 |
| 29 | 52.5 | 5.85 | 52.1 |
| 30 | 42.9 | 6.50 | 51.4 |
| 31 | 65.3 | 5.25 | 60.0 |
| 32 | 55.4 | 5.65 | 53.5 |
| 33 | 52.6 | 5.90 | 52.1 |
| 39 | 37.8 | 6.80 | 42.4 |
| 56 | 40.7 | 6.55 | 45.4 |
| 60 | 39.0 | 6.65 | 44.2 |
| 66 | 47.9 | 6.35 | 49.6 |
| 71 | 46.3 | 6.30 | 48.8 |
| 77 | 47.3 | 6.40 | 49.3 |
| Edaravone (trade name) | 37.3 | 6.10 | 42.6 |
| Control group | — | 8.35 | 17.3 |

According to the present example, the compounds of the present invention demonstrated efficacy greater than or equal to that of the existing drug Edaravone (trade name) with respect to cerebral infarction reduction rate, improvement of neurological symptoms and improvement of motor function, and was clearly demonstrated to be useful as a therapeutic agent for cerebrovascular diseases.

Example 14

Injection Solution Containing 3 mg 3 mg of Compound 29 were dissolved in 2 ml of physiological saline for injection followed by aseptically filling into an ampule.

Example 15

Pharmacological Study Using an Ouabain-Induced Arrhythmia Model in Guinea Pigs

In order to demonstrate the therapeutic action on heart disease of compounds of the present invention, a pharmacological study was conducted using an ouabain-induced arrhythmia model, which is widely used for the pharmacological evaluation of antiarrhythmics, for the compounds used in Example 1 (Compilation of Uses of Animal Models for New Drug Development, R&D Planning, 166, 1985).

After guinea pigs (Hartley strain, age 6 weeks) were anesthetized with urethane, induction electrodes were attached to the hind limbs and fore limbs, and standard 2-lead electrocardiograms were monitored with an animal electrocardiogram analysis system (ECG-01, Japan Energy). After confirming that the waveforms of the electrocardiogram and heart rate were within the normal range, an incision was made in the epidermis of the neck followed by inserting a breathing tube into the trachea and cannulating a polyethylene tube into the left external jugular vein and left common carotid artery.

Immediately after administering a compound of the present invention dissolved in a physiological saline solution into the right external jugular vein, ouabain was continuously infused at 3 μg/0.1 ml/min through the cannulated polyethylene tube into the left external jugular vein using a syringe pump (Atom Syringe Pump 1235 (trade name), Atom Medical Corporation).

In addition, the polyethylene tube cannulated in the left common carotid artery was connected to a pressure transducer (P23XL, Gould Electronics), and fed to a pressure processor signal conditioner (TA-11, Gould Electronics) to record blood pressure and heart rate on a thermal plate recorder.

The results were assessed by comparing the dose (μg/kg) of ouabain administered until the appearance of arrhythmia and occurrence of cardiac arrest (arrhythmia is not induced even if a large dose of ouabain is administered if antiarrhythmic effects are high). Furthermore, a solvent dose group (administered only physiological saline in an amount equal to that of the test drug groups), and a positive control group administered a typical antiarrhythmic disopyramide phosphate (physiological saline solution), were also provided. The test results are shown in Table 6.

TABLE 6

| Compound | Dose (mg/kg) | Ouabain (μg/kg) | |
|---|---|---|---|
| | | Arrhythmia | Cardiac arrest |
| 3 | 3 | 169 | 235 |
| 9 | 3 | 170 | 245 |
| 27 | 3 | 180 | 258 |
| 28 | 3 | 173 | 267 |
| 29 | 3 | 170 | 254 |
| 30 | 3 | 173 | 247 |
| 31 | 3 | 179 | 259 |
| 32 | 3 | 176 | 243 |
| 33 | 3 | 171 | 239 |
| 39 | 3 | 165 | 229 |
| 56 | 3 | 172 | 244 |
| 60 | 3 | 170 | 243 |
| 66 | 3 | 168 | 237 |
| 71 | 3 | 171 | 239 |
| 77 | 3 | 167 | 227 |
| Disopyramide phosphate | 3 | 175 | 247 |
| Physiological saline dose group | — | 132 | 176 |

As shown in Table 6, in the solvent dose group, arrhythmia was induced at a total continuously infused dose of ouabain of 132 μg/kg, after which cardiac arrest occurred at a dose of 176 μg/kg. In contrast, the threshold values for inducing arrhythmia and cardiac arrest by ouabain were increased by administration of the typical antiarrhythmic, disopyramide phosphate at 3.9 mg/kg (3.0 mg/kg as disopyramide), with arrhythmia and cardiac arrest occurring at 175 μg/kg and 247 μg/kg, respectively, thereby confirming the antiarrhythmic action of disopyramide phosphate.

On the other hand, during administration of compounds of the present invention, increases in the threshold values for inducing arrhythmia and cardiac arrest were observed to be equal to or greater than those of disopyramide phosphate.

As indicated by the present example, compounds of the present invention have antiarrhythmic action equal to or greater than that of commercially available antiarrhythmics, and are useful as therapeutic agents for heart disease.

Example 16

Study of Arrhythmia-Inducing Action in Guinea Pigs

Many therapeutic agents for heart disease, and particularly antiarrhythmics, demonstrate cardiotoxicity, and the disopyramide phosphate used as a positive control in Example 2 is also known to have pro-arrhythmogenic action despite having antiarrhythmic action (Japan Pharmaceutical Reference, 5th edition, Osaka Prefecture Hospital Pharmaceutical Association, 543, 1992).

In this example, the occurrence of arrhythmia or cardiac arrest was observed up to 1 hour after administration of disopyramide phosphate or compounds of the present invention without administering ouabain using the same procedure as Example 2. The results of the study are shown in Table 7.

TABLE 7

| Compound | Dose (mg/kg) | Occurrence of Arrhythmia | Occurrence of cardiac arrest |
|---|---|---|---|
| 3 | 3 | No | No |
| 3 | 10 | No | No |
| 9 | 3 | No | No |
| 9 | 10 | No | No |
| 27 | 3 | No | No |
| 27 | 10 | No | No |
| 28 | 3 | No | No |
| 28 | 10 | No | No |
| 29 | 3 | No | No |
| 29 | 10 | No | No |
| 30 | 3 | No | No |
| 30 | 10 | No | No |
| 31 | 3 | No | No |
| 31 | 10 | No | No |
| 32 | 3 | No | No |
| 32 | 10 | No | No |
| 33 | 3 | No | No |
| 33 | 10 | No | No |
| 39 | 3 | No | No |
| 39 | 10 | No | No |
| 56 | 3 | No | No |
| 56 | 10 | No | No |
| 60 | 3 | No | No |
| 60 | 10 | No | No |
| 66 | 3 | No | No |
| 66 | 10 | No | No |
| 71 | 3 | No | No |
| 71 | 10 | No | No |
| 77 | 3 | No | No |
| 77 | 10 | No | No |
| Disopyramide phosphate | 3.9 | No | No |
| Disopyramide phosphate | 12.9 | — | Yes |

As shown in Table 7, since cardiac arrest occurred immediately after administration of disopyramide phosphate at 12.9 mg/kg (10 mg/kg as disopyramide) without having time to examine for the presence of arrhythmia, the range between the therapeutic dose and the toxic dose was extremely narrow. In contrast, cardiotoxicity was not observed for any of the compounds of the present invention at doses of 3 or 10 mg/kg, thus demonstrating that the compounds of the present invention are safe even at a dose of 10 mg/kg, which is roughly three times the dose of 3 mg/kg at which efficacy is demonstrated.

Example 17

Pharmacological Study Using a Model of Myocardial Ischemia-Reperfusion Injury in Dogs In order to confirm the efficacy of compounds of the present invention on myocardial infarction and arrhythmia caused by myocardial infarction, a pharmacological study was conducted using a model of myocardial ischemia reperfusion injury in dogs for the compounds used in Example 1.

Dogs having body weights of approximately 10 kg were anesthetized with pentobarbital (trade name) (30 mg/ml/kg) followed by shaving the surgical site after starting artificial respiration. The femoral vein and femoral artery were separated followed by cannulation. The femoral vein was used as the administration route for the test substances, while the femoral artery was used to measure blood pressure.

Next, after opening the left chest, making an incision in the pericardium and exposing the left ventricle, the left coronary artery was separated. A silk suture was passed through the coronary artery to occlude, followed by the attachment of an electromagnetic flow meter probe for measuring blood flow.

In addition, a pair of ultrasound crystal probes was fixed in position to measure changes in ventricular wall length as a indicator of myocardial contractile force, and indwelling needle was installed for measuring left intraventricular pressure. Compounds of the present invention were administered into the femoral vein at 3 mg/kg (15% physiological saline solution) followed 10 minutes later by occluding the coronary artery for 20 minutes, and subsequently reperfusing the coronary artery. Myocardial contraction following ischemia-reperfusion was compared for each group based on a value of 100 for myocardial contraction prior to ischemic reperfusion. In addition, comparisons were also made with a solvent control group administered only physiological saline. The study results are shown in Table 8.

TABLE 8

| Compound | Dose (mg/kg) | Myocardial Contraction (%) (Based on a value of 100% for prior to ischemia-reperfusion) |
|---|---|---|
| 3 | 3 | 81 |
| 9 | 3 | 78 |
| 27 | 3 | 85 |
| 28 | 3 | 76 |
| 29 | 3 | 80 |
| 30 | 3 | 77 |
| 31 | 3 | 89 |
| 32 | 3 | 79 |
| 33 | 3 | 82 |
| 39 | 3 | 74 |
| 56 | 3 | 71 |
| 60 | 3 | 88 |
| 66 | 3 | 80 |
| 71 | 3 | 72 |
| 77 | 3 | 75 |
| Solvent dose group | — | 41 |

As shown in Table 8, myocardial contraction decreased to 41% due to injury caused by ischemia-reperfusion in the solvent dose group (non-drug dose group). In contrast, in those groups dosed with compounds of the present invention, myocardial contraction was 71 to 89% of that prior to ischemic reperfusion, thus clearly demonstrating a reduction in the degree of myocardial injury due to ischemia-reperfusion. The model used in this study is an experimental model of myocardial injury accompanying myocardial infarction and clinically serious myocardial injury due to reperfusion of blood flow into the myocardial region (Compilation of Uses of Animal Models for New Drug Development, R&D Planning, 166, 1985). On the basis of the findings in the present example, the compounds of the present invention were clearly demonstrated to be heart disease therapeutic agents useful for the treatment of myocardial infarction and myocardial injury accompanying myocardial infarction.

Example 18

Pharmacological Study Using a Model of Myocardial Ischemia-Reperfusion Injury in Rats A pharmacological study was conducted using a model of myocardial ischemia-reperfusion injury in rats for the compounds used in Example 1.

The animals were held in the dorsal position under anesthesia by intraperitoneal administration of sodium pentobarbital at dose of 55 mg/kg, an incision was made in the neck, and an artificial respiration tube was inserted into the trachea followed by operation of an artificial respirator (SN-480-7, Shinano) (1.5 mL/100 g: 50 times/min). Blood pressure was monitored by inserting a blood pressure monitoring cannula into the left femoral artery using a pressure transducer (TP-400T, Nihon Kohden) and a pressure strain gauge (AP-610G, Nihon Kohden).

In addition, a cannula for administration of the test substances was inserted into the left femoral vein, and 2-lead electrocardiograms were recorded with an electrocardiograph (JB-101J, AB-651J, Nihon Kohden) by attaching electrodes to the fore limbs and hind limbs. Heart rate was measured with an electrocardiograph (AT-601G, Nihon Kohden) based on the pulse pressure waveform, while body temperature was maintained at 36.5±0.5° using a warming mat.

Next, the chest was opened at the fifth intercostal space, and an incision was made in the pericardium to expose the heart. The heart was then exteriorized from the thoracic cavity using a ring-shaped forceps, and a threaded suture needle was inserted into cardiac muscle of the pulmonary artery conus, the thread was passed under the descending branch of the left coronary artery, and the heart was immediately returned to the thoracic cavity. Preparations for ligation were made by passing this thread through a polyethylene tube.

After confirming that blood pressure and heart rate had stabilized for approximately 20 minutes, the test substances were administered intravenously. Five minutes later, the coronary artery was ligated for 5 minutes by clamping the polyethylene tube with a mosquito forceps. Following ligation, blood flow was reperfused, the appearance of ventricular tachycardia and ventricular fibrillation was monitored for 5 minutes and the animals were observed for survival. Using 8 rats per group, compounds of the present invention and lidocaine were administered at does of 3 mg/kg of body weight (2 mL), while mL of physiological saline was administered for a control group. The study results are shown in Table 9.

TABLE 9

| Compound | Incidence of Ventricular Tachycardia (%) | Incidence of Ventricular Fibrillation (%) | Mortality Rate (%) |
|---|---|---|---|
| 3 | 62.5 | 12.5 | 0 |
| 9 | 75.0 | 25.0 | 12.5 |
| 27 | 50.0 | 0 | 0 |
| 28 | 62.5 | 12.5 | 12.5 |
| 29 | 62.5 | 12.5 | 12.5 |
| 30 | 62.5 | 12.5 | 12.5 |
| 31 | 37.5 | 0 | 0 |
| 32 | 50.0 | 12.5 | 12.5 |
| 33 | 50.0 | 12.5 | 0 |
| 39 | 62.5 | 12.5 | 12.5 |
| 56 | 62.5 | 12.5 | 25.0 |
| 60 | 62.5 | 25.0 | 0 |
| 66 | 62.5 | 12.5 | 12.5 |
| 71 | 62.5 | 12.5 | 0 |
| 77 | 75.0 | 12.5 | 12.5 |
| Lidocaine | 62.5 | 12.5 | 12.5 |
| Physiological Saline Dose Group | 100 | 100 | 87.5 |

As shown in Table 9, ventricular tachycardia and ventricular fibrillation caused by ischemia-reperfusion injury appeared in 100% of the animals of the solvent dose group (control group), and this group showed a high mortality rate of 87.5%. In addition, inhibitory effects were observed in the lidocaine dose group serving as a positive control, showing values of 62.5%, 12.5% and 12.5%, respectively.

In contrast, effects equal to or greater than those of the lidocaine dose group serving as the positive control were observed in groups dosed with compounds of the present invention, thereby clearly demonstrating that compounds of the present invention are heart disease therapeutic agents useful for treatment of myocardial infarction and myocardial injury accompanying myocardial infarction.

Example 19

5% Powder 50 mg of crystals of Compound 27 shown in Table 1 were pounded in a mortar followed by the addition of 950 mg of lactose and mixing well while pounding in the mortar to obtain a 5% powder.

Example 20

10% Granules 300 mg of Compound 27 shown in Table 1 were mixed and pounded with 300 mg of starch in a mortar. 2000 mg of lactose were added to this mixture followed by the addition of 370 mg of starch and mixing. Separate from this, 1 mL of purified water was added to 30 mg of gelatin followed by heating and dissolution. After cooling, 1 mL of ethanol was added while stirring to prepare a gelatin liquid. This gelatin liquid was added to the previously prepared mixture followed by kneading, granulating and drying to obtain granules.

Example 21

0.1% Injection Preparation 10 mg of Compound 31 shown in Table 1 were dissolved in distilled water for injection to bring to a final volume of 10 mL followed by aseptically filling into ampules.

INDUSTRIAL APPLICABILITY

A novel quaternary ammonium compound of the present invention can be used therapeutically as, for example, a pharmaceutical, and particularly as a therapeutic agent for cerebrovascular disorder, alleviant thereof and therapeutic agent for heart disease.

The invention claimed is:

1. A quaternary ammonium compound represented by general formula (I) or (I'):

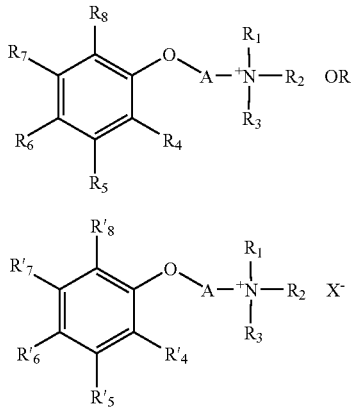

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$ to $R_3$ may be the same or different and represent a linear or branched alkyl group having 1 to 12 carbon atoms, one of $R_4$ to $R_8$ represents $CO_2^-$ or $SO_3^-$, while no more than three of the remaining $R_4$ to $R_8$ represent a group selected from the group consisting of a hydroxyl group and an alkoxy group having 1 to 4 carbon atoms, and other $R_4$ to $R_8$ represent a hydrogen atom, one of $R'_4$ to $R'_8$ represents $CO_2H$ or $SO_3H$, while no more than three of the remaining $R'_4$ to $R'_8$ represent a group selected from a protected hydroxyl group and an alkoxy group having 1 to 4 carbon atoms, while other $R'_4$ to $R'_8$ represent a hydrogen atom, and $X^-$ represents chlorine ion, bromine ion, iodine ion, hydroxide ion, formate anion, acetate anion, propionate anion, methanesulfonate anion, p-toluenesulfonate anion, oxalate anion, succinate anion, maleate anion, phthalate anion, carbonate ion, sulfate ion, nitrate ion or phosphate ion).

2. A quaternary ammonium compound according to claim 1, wherein one of $R_4$ to $R_8$ is $CO_2^-$, or one of $R'_4$ to $R'_8$ is $CO_2H$.

3. A quaternary ammonium compound according to claim 1, wherein one of $R_4$ to $R_8$ is $SO_3^-$, or one of $R'_4$ to $R'_8$ is $SO_3H$.

4. A quaternary ammonium compound according to claim 2, wherein one of the remaining $R_4$ to $R_8$ or one of the remaining $R'_4$ to $R'_8$ is a hydroxyl group.

5. A quaternary ammonium compound according to claim 3, wherein one of the remaining $R_4$ to $R_8$ or one of the remaining $R'_4$ to $R'_8$ is a hydroxyl group.

6. A quaternary ammonium compound according to claim 4, wherein A is a linear alkyl group having 2 carbon atoms.

7. A quaternary ammonium compound according to claim 5, wherein A is a linear alkyl group having 2 carbon atoms.

8. A quaternary ammonium compound according to claim 6, wherein $R_1$ to $R_3$ are methyl groups.

9. A quaternary ammonium compound according to claim 7, wherein $R_1$ to $R_3$ are methyl groups.

10. A process for producing a quaternary ammonium compound represented by general formula (I):

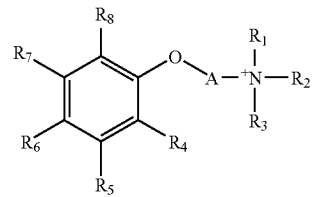

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$, $R_2$ and $R_3$ may be the same or different and represent a linear or branched alkyl group having 1 to 12 carbon atoms, one of $R_4$ to $R_8$ represents $CO_2^-$ or $SO_3^-$, while no more than three of the remaining $R_4$ to $R_8$ represent a group selected from the group consisting of a hydroxyl group and an alkoxy group having 1 to 4 carbon atoms, and other $R_4$ to $R_8$ represent a hydrogen atom) comprising: reacting with a phenol derivative represented by general formula (II):

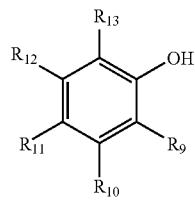

(wherein, one of $R_9$ to $R_{13}$ represents a carboxyl group protected or a sulfonic acid group by an ester group, no more than three of the remaining $R_9$ to $R_{13}$ represent a group selected from the group consisting of a protected hydroxyl group and an alkoxy group having 1 to 4 carbon atoms, and other $R_9$ to $R_{13}$ represent a hydrogen atom) a sulfonic acid ester derivative represented by general formula (III):

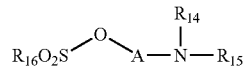

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_{14}$ to $R_{15}$ may be the same or different and represent a linear or branched alkyl group having 1 to 12 carbon atoms, and $R_{16}$ represents a lower alkyl group having 1 to 4 carbon atoms or an aryl group having 6 to 7 carbon atoms) in an organic solvent and in the presence of a basic substance, to obtain a an amino compound represented by general formula (IV):

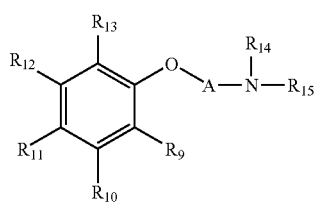

(IV)

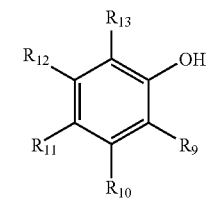

(II)

(wherein, one of $R_9$ to $R_{13}$ represents a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, and other $R_9$ to $R_{13}$ represent a hydrogen atom) a sulfonic acid ester derivative represented by general formula (III):

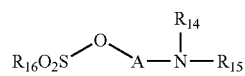

(III)

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, one of $R_9$ to $R_{13}$ represents a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, other $R_9$ to $R_{13}$ represent a hydrogen atom, and $R_{14}$ to $R_{15}$ may be the same or different and represent a linear or branched alkyl group having 1 to 12 carbon atoms), and a linear or branched alkyl halide having 1 to 12 carbon atoms or a sulfonic acid ester esterified by a linear or branched alkyl group having 1 to 12 carbon atoms is reacted with a compound represented by general formula (IV), followed by deprotecting the carboxyl group or the sulfonic acid group protected by an ester group, and the protected hydroxyl group, and treating with an ion exchange resin.

11. A process for producing a quaternary ammonium compound represented by general formula (I'):

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_{14}$ to $R_{15}$ may be the same or different and represent a linear or branched alkyl group having 1 to 12 carbon atoms, and $R_{16}$ represents a lower alkyl group having 1 to 4 carbon atoms or an aryl group having 6 to 7 carbon atoms) in an organic solvent and in the presence of a basic substance, to obtain a an amino compound represented by general formula (IV):

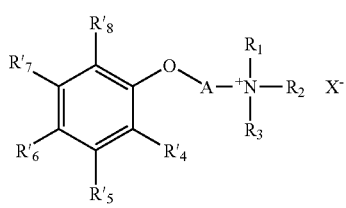

(I')

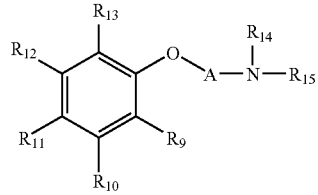

(IV)

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, $R_1$, $R_2$ and $R_3$ may be the same or different and represent a linear or branched alkyl group having 1 to 12 carbon atoms, one of $R_{14}$ to $R_{18}$ represents $CO_2H$ or $SO_3H$, while no more than three of the remaining $R'_4$ to $R'_8$ represent a group selected from the group consisting of a hydroxyl group and an alkoxy group having 1 to 4 carbon atoms, other $R'_4$ to $R'_8$ represent a hydrogen atom, and $X^-$ represents an anion capable of forming a salt with a quaternary ammonium group) comprising: reacting with a phenol derivative represented by general formula (II):

(wherein, A represents a linear alkyl group having 1 to 4 carbon atoms, a branched alkyl group having 2 to 4 carbon atoms, a linear alkyl group having 1 to 4 carbon atoms and a hydroxyl group, or a branched alkyl group having 2 to 4 carbon atoms and a hydroxyl group, one of $R_9$ to $R_{13}$ represent a carboxyl group or a sulfonic acid group protected by an ester group, no more than three of the remaining $R_9$ to $R_{13}$ represent a group selected from the group consisting of a protected hydroxyl group and an alkoxy group having 1 to 4 carbon atoms, other $R_9$ to $R_{13}$ represent a hydrogen atom, and $R_{14}$ to $R_{15}$ may be the same or different and represent a linear or branched alkyl group having 1 to 12 carbon atoms), and a linear or branched alkyl halide having 1 to 12 carbon atoms or a sulfonic acid ester esterified by a linear or branched alkyl group having 1 to 12 carbon atoms is reacted with a compound represented by general formula (IV), followed by deprotecting the carboxyl group or the sulfonic acid group protected by an ester group, and the protected hydroxyl group, and treating with an acidic substance.

12. A process for producing a quaternary ammonium compound represented by general formula (I) or (I') according to claim 10, wherein the organic solvent used in the step for reacting a sulfonic acid ester derivative represented by general formula (III) with a phenol derivative represented by general formula (II) is an alcohol, ether or amide organic solvent.

13. A process for producing a quaternary ammonium compound represented by general formula (I) or (I') according to claim 12, wherein $R_{16}$ of general formula (III) is a methyl group.

14. A process for producing a quaternary ammonium compound represented by general formula (I) or (I') according to claim 13, wherein the organic solvent used in the step for reacting a sulfonic ester derivative represented by general formula (III) with a phenol derivative represented by general formula (II) is an ether organic solvent having 4 to 6 carbon atoms.

15. A treatment method for a cerebrovascular disease comprising administering to a mammal in need thereof a quaternary ammonium compound according to claim 1.

16. A treatment method for a heart disease comprising administering to a mammal in need thereof a quaternary ammonium compound according to claim 1.

17. A pharmaceutical composition comprising a quaternary ammonium compound according to claim 1.

18. The method of claim 15, wherein the cerebrovascular disease is cerebral infarction, cerebral thrombosis, cerebral embolism, transient ischemic attack or a functional disorder caused by these diseases.

* * * * *